United States Patent
Welp et al.

(10) Patent No.: US 7,109,378 B2
(45) Date of Patent: Sep. 19, 2006

(54) MONOLITH CATALYTIC REACTOR COUPLED TO STATIC MIXER

(75) Inventors: Keith Allen Welp, Macungie, PA (US); Anthony Rocco Cartolano, Orefield, PA (US); David Joseph Parrillo, Schenectady, NY (US); Richard Peter Boehme, Allentown, PA (US); Reinaldo Mario Machado, Allentown, PA (US); Sylvia Caram, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 566 days.

(21) Appl. No.: 10/053,787

(22) Filed: Jan. 21, 2002

(65) Prior Publication Data
US 2003/0049185 A1 Mar. 13, 2003

Related U.S. Application Data

(63) Continuation-in-part of application No. 09/942,839, filed on Aug. 30, 2001, now abandoned.

(51) Int. Cl.
*C07C 209/30* (2006.01)
*C07C 209/32* (2006.01)
*C07C 209/34* (2006.01)
*C07C 209/48* (2006.01)
*C07C 209/52* (2006.01)

(52) U.S. Cl. .................. 564/417; 564/418; 564/420; 564/421; 564/422; 564/423; 564/489; 564/493; 422/129; 422/187; 422/224

(58) Field of Classification Search ............... 564/417, 564/418, 420, 421, 422, 423, 489, 493; 422/129, 422/187, 224
See application file for complete search history.

(56) References Cited

U.S. PATENT DOCUMENTS

| | | | |
|---|---|---|---|
| 4,428,922 A | 1/1984 | Hopkins et al. | 423/588 |
| 4,552,748 A | 11/1985 | Berglin et al. | 423/588 |
| 5,063,043 A | 11/1991 | Bengtsson et al. | 423/588 |
| 5,478,535 A | 12/1995 | Fierz et al. | 422/198 |
| 5,688,047 A | 11/1997 | Signer et al. | 366/337 |
| 5,763,687 A | 6/1998 | Morisaki et al. | 568/924 |
| 5,779,995 A | 7/1998 | Witt et al. | 422/224 |
| 5,817,901 A | 10/1998 | Trambouze et al. | |
| 6,005,143 A * | 12/1999 | Machado et al. | 564/423 |
| 6,242,649 B1 | 6/2001 | Beckhaus et al. | 564/416 |
| 6,267,912 B1 | 7/2001 | Asakuea et al. | |
| 6,521,791 B1 * | 2/2003 | Welp et al. | 564/423 |
| 6,800,773 B1 | 10/2004 | Reesink et al. | |
| 2002/0000067 A1 | 1/2002 | Koichi et al. | |

FOREIGN PATENT DOCUMENTS

| | | |
|---|---|---|
| DE | 19844901 | 9/1998 |
| DE | 198 58 974 A | 6/2000 |
| EP | 0233642 | 8/1987 |
| EP | 0 638 357 A | 2/1995 |
| EP | 0 995 489 A | 4/2000 |
| JP | 55 047127 A | 6/1980 |
| WO | WO 9855216 | 12/1998 |
| WO | WO 0035852 | 6/2000 |

OTHER PUBLICATIONS

Grosz–Röll, F., J. Bättig and F. Moser, of Koch Engineering Company, Inc. entitled, "Gas/Liquid Mass Transfer with Static Mixing Units", Fourth European Conference on Mixing, Apr. 27–29, 1982 pp 225–236.

Heiszwolf, Johan J., et al., "Hydrodynamic Aspects of the Monolith Loop Reactor", Chemical Engineering Science 56 (2001) 805–812.

Patrick, Robert H., et al. "Residence Time Distribution in Three–Phase Monolith Reactor" AIChe Journal, Mar. 1995, vol. 41, No. 3, pp 649–657.

Kawakami, Koei, et al., "Performance of a Honeycomb Monolith Bioreactor in a Gas–Liquid–Solid Three–Phase System", Ind. Eng. Chem. Res. 1989, 28, 394–400.

Hatzlantoniou, Vasillos and Andersson, Bengt, "The Segmented Two–Phase Flow Monolithic Catalyst Reactor. An Alternative for Liquid–Phase Hydrogenations", Ind. Eng. Chem. Fundam. 1981, 23, 82–88.

Hatzlantoniou, Vasillos, Andersson, Bengt, and Schoon, Nils–Herman, "Mass Transfer and Selectivity in Liquid–Phase Hydrogenation fo Nitro Compounds in a Monolithic Catalyst Reactor with Segmented Gas–Liquid Flow", Ind. Eng. Chem, Process Des. Dev., 1988, 25, 964–970.

Irandoust, Said and Andersson, Bengt; Department of Chemical Reaction Engineering, Chalmers University of Technology, S–412 96 Gothenburg, Sweden and Bengtsson, Erik and Siverstrom; EKA Nobel AB, S–445 01 Surte, Sweden, "Scaling Up a Monolithic Catalyst Reactor with Two–Phase Flow", Ind. Eng. Chem. Res., 1989, 28, 1489–1493.

Irandoust, Said and Andersson, Bengt, "Mass Transfer and Liquid–Phase Reactions in a Segmented Two–Phase Flow Monolithic Catalyst Reactor", Chemical Engineering Science, vol. 43, No. 8, pp. 1983–1988.

XP002264241 (Abstract) Sep. 7, 1991,Sinion Soviet–Italian Petrochem Co.

* cited by examiner

*Primary Examiner*—Peter G. O'Sullivan
(74) *Attorney, Agent, or Firm*—Russell L. Brewer; Mary E. Bongiorno

(57) ABSTRACT

The invention pertains to an improved apparatus comprised of a monolith catalytic reactor having an inlet and an outlet and a static mixer having an inlet and an outlet thereto with the outlet of said static mixer in communication with the inlet of said monolith catalytic reactor. The invention also pertains to an improvement in a process for effecting a reaction in the monolith catalytic reactor wherein a reactant gas and reactant liquid are introduced to the inlet to the monolith catalytic reactor, reacted and, then, the reaction product passed through the outlet of the monolith catalytic reactor.

12 Claims, 3 Drawing Sheets

MONOLITH CATALYTIC REACTOR COUPLED TO STATIC MIXER

CROSS REFERENCE TO RELATED APPLICATIONS

This is a continuation in part of application Ser. No. 09/942,839 filed on Aug. 30, 2001, now abandoned.

BACKGROUND OF THE INVENTION

Industrial reactions between reactant gases and liquids such as those involving hydrogenation of unsaturated organic compounds and those having functional groups capable of condensation are often performed by using finely divided powdered slurry catalysts in stirred-tank reactors. These slurry phase reaction systems are inherently problematic in chemical process safety, operability and productivity. The finely divided, powdered catalysts are often pyrophoric and require extensive operator handling during reactor charging and filtration. By the nature of their heat cycles for start-up and shut-down, slurry systems promote co-product formation which can shorten catalyst life and lower yield to the desired product.

An option to the use of finely divided powder catalysts in stirred reactors has been the use of pelleted catalysts in fixed bed reactors. While this reactor technology does eliminate much of the handling and waste problems, a number of engineering challenges have not permitted the application of fixed bed reactor technology to the reaction of gases with liquid organic compounds. Controlling the overall temperature rise and temperature gradients in the reaction process has been one problem. A second problem is that in fixed bed packed reactors there is a significant pressure drop due to the high flow rates required for hydrogenation. A third problem is that liquid-gas distribution is problematic thus often leading to poor conversion and localized concentration gradients.

Monolith catalytic reactors are an alternative to fixed bed reactors and have a number of advantages over conventional fixed bed reactors. These reactors have low pressure drop which allow them to be operated at higher gas and liquid velocities. These higher velocities of gas and liquids promote high mass transfer and mixing and the parallel channel design of a monolith inhibits the coalescence of the gas in the liquid phase.

The following patents and articles are illustrative of the prior art as they relate to gas/liquid reaction.

U.S. Pat. No. 5,763,687 discloses apparatus designed for the preparation of aromatic mononitro compounds. The reactor comprises a tube containing more than one twisted tabular member aligned in sequence, so that a front margin of one twisted tabular member is substantially perpendicular to a back margin of the preceding member. Preferably the reactor comprises a tube and a hollow tube without tabular members therein.

Patrick et al, AICHE Journal, Vol.41, No. 3 (March 1995) disclose a monolith reactor of uncoated cordierite and its use to determine residence time distribution and in designing gas/liquid phase reactions. Liquid and gas are introduced upflow through the monolith reactor with the reactant gas being passed through a porous glass frit. Gas bubbles generated by passage of gas through the glass frit are typically larger than the width of the monolith channels.

U.S. Pat. No. 6,005,143 relates to an improvement in a process for hydrogenating a nitroaromatic composition namely dinitrotoluene by contacting the dinitrotoluene with hydrogen in a reactor employing a monolith catalytic reactor system. Broadly the improvement resides in the continuous, essentially solventless, adiabatic hydrogenation of dinitrotoluene to toluenediamine in a monolith catalytic reactor operating in plug flow.

U.S. Pat. No. 4,428,922 discloses a method for manufacturing hydrogen peroxide in a fixed bed catalytic hydrogenator by utilizing a static mixer to premix hydrogen with the liquid prior to reaction in a fixed bed catalytic reactor.

U.S. Pat. No. 4,552,748 discloses a process for the production of hydrogen peroxide by passing a working solution and hydrogen upflow through a reactor comprised of parallel channels having a catalytically active material attached thereto. Reaction product is withdrawn from the upper portion of the reactor and recycled.

U.S. Pat. No. 5,688,047 discloses a static mixer with mixing elements. It is comprised of a tube and a mixing element rotated at an angle of 90° about the tube axis.

BRIEF SUMMARY OF THE INVENTION

The invention pertains to an apparatus comprised of a monolith catalytic reactor having an inlet and an outlet and a static mixer having an inlet and an outlet with the outlet of said static mixer in communication with the inlet of said monolith catalytic reactor. The invention also pertains to an improvement in a process for effecting reaction between a reactant gas and reactant liquid in a monolith catalytic reactor. The improvement to the process resides in introducing the reactant gas and reactant liquid to the inlet of a static mixer, mixing the reactant gas and reactant liquid therein, discharging the resulting mixed reactant gas and reactant liquid through the outlet of the static mixer to the inlet of the monolith catalytic reactor and, then, reacting the resulting mixture of reactant gas and reactant liquid. The mixture of reactant gas and reactant liquid when passed upflow through the monolith catalytic reactor has particular safety advantages in the hydrogenation of dinitrotoluene.

There are significant advantages to the apparatus and process and these include:

- an ability to enhance mass transfer of reactant gas and reactant liquid in the monolith catalytic reactor;
- an ability to provide for a short reactant contact time thereby minimizing byproduct formation, and also minimizing concern about degradation of reactant, reaction product or byproduct if high concentration regions are established;
- an ability to control reactant gas bubble size necessary to achieve Taylor flow in the monolith catalytic reactor on a consistent basis;
- an ability to provide substantially even distribution of a frothy gas/liquid mixture to the entire cross-section of the monolith catalytic reactor
- an ability to enhance reaction rate and thereby enhance productivity; and,
- an ability to enhance throughput and efficiency of the monolith catalytic reactor,

DETAILED DESCRIPTION OF THE INVENTION

Figure 1:
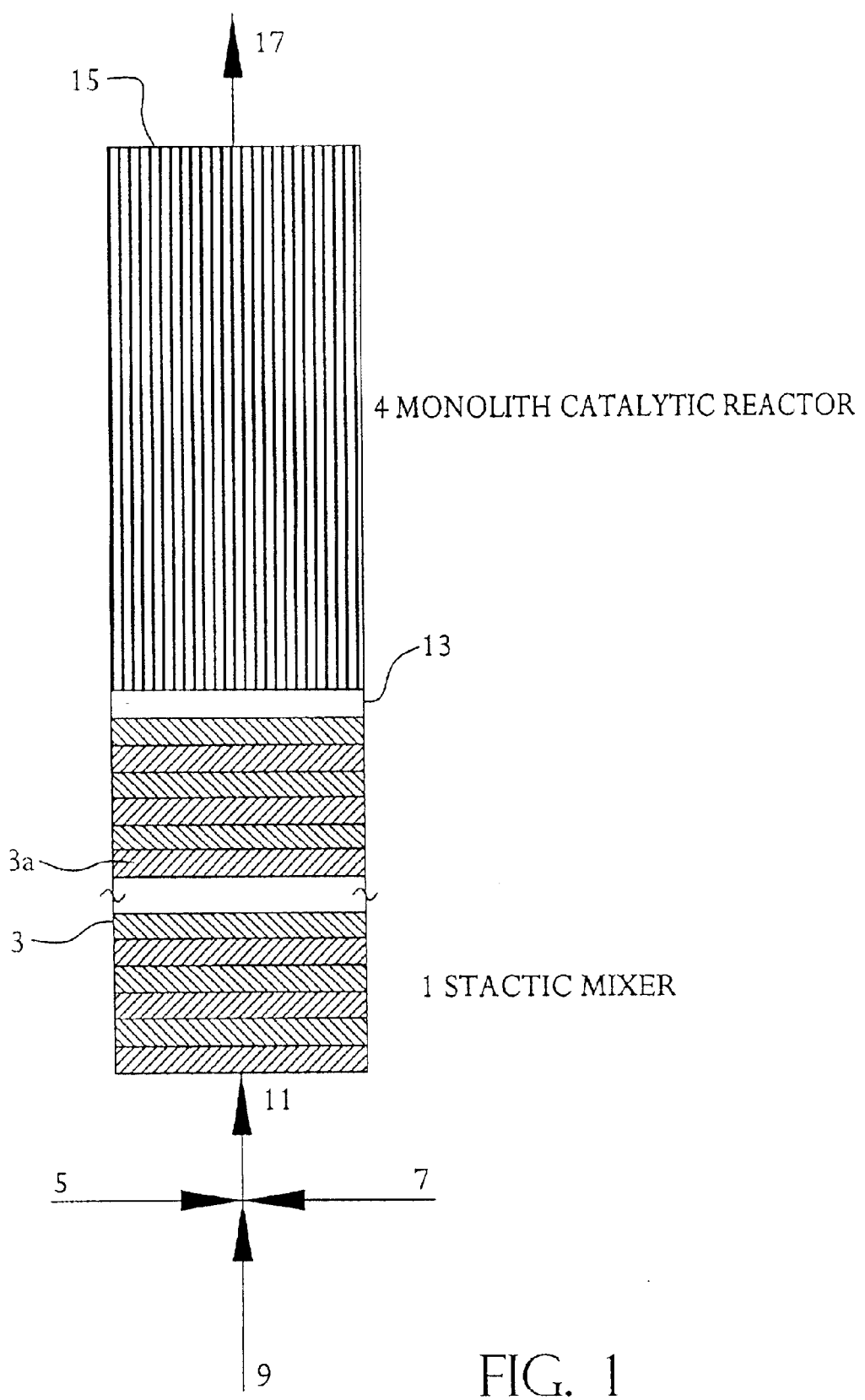
FIG. 1 is a view in cross-section of a static mixer coupled to a monolith catalytic reactor.

One aspect of the invention relates to an improvement in an apparatus for gas/liquid reactions utilizing a monolith catalytic reactor, particularly those suited for industrial application, e.g., those having a diameter of from 2–8 feet. The improvement in the apparatus resides in coupling the outlet of a static mixer to the inlet of a monolith catalytic reactor. In terms of process operation, reactant gas and reactant liquid are introduced to the inlet of the static mixer and passed upflow therethrough, mixed, removed via the outlet of the static mixer, and, then, charged to the inlet of the monolith catalytic reactor. Reaction between the reactant gas and reactant liquid takes place in the monolith catalytic reactor and reaction product is withdrawn from the outlet of the monolith catalytic reactor. Often a portion of the reaction product containing unreacted gas and liquid is combined with the feed reactant gas and reactant liquid and recycled through the monolith catalytic reactor system.

Much of the background art attempting to use monolith catalysts in fixed bed reactors have utilized downward flow. It has been found though that this flow direction can result in stagnant or reverse flow at some flow velocities, particularly those required in startup. Such flow behavior makes a downward flow process undesirable for reactions such as the conversion of dinitrotoluene to toluenediamine. Conditions in the reactor may result in a runaway reactor. However, passing the reactant gas and dinitrotoluene reactant liquid upflow through the static mixer and monolith reactor assures a stable froth flow from the static mixer and stable Taylor flow through the monolith channels of the reactor and thereby minimizes the chance for a runaway reaction.

Static mixers are known and are typically comprised of parallel plates interposed at an angle to each other. More particularly, they are comprised of a plurality of sections comprised of a tubular housing having a flow direction along an axis carrying stationary, rigid elements that form interengaging and intersecting channels in the flow direction. These channels define a tortuous pathway from inlet to outlet of the tubular housing. This pathway is designed so that the interengaging and intersecting channels effect a splitting of the fluid streams, a rearranging of the fluid streams and then a combining of these streams as the fluids pass through the tubular housing. The angles at which the alternating parallel channels intersect may vary but typically such angles are within a range of from 45 to 90 degrees.

One type of static mixer is comprised of a tubular housing having a wall, an axis and a flow direction, the axis dividing the interior of the housing into longitudinally extending first and second interior housing sectors. A mixing element includes at least two mixing sections with one of the sections disposed in a housing sector. The flow direction in the mixing sections are defined by parallel, spaced apart strips extending in the flow direction nonparallel to the housing axis. Once the fluid contacts the wall surface it is allowed to flow upward to the next parallel strip and directed in an opposite flow nonparallel to the axis.

The shape of the walls of the rigid elements defining the channels can vary and some are in the form of corrugations, waffles, or they may be straight. The channels conduct liquid and gas radially outward in the static mixer and then radially inward whereby at intersection points these fluids contact which other and fragmentation takes place. Typically a static mixer is combined of a plurality of each section and the sections rotated typically at 45 to 90° increments with respect to the longitudal axis, as shown by the directional arrows in FIG. 2, with respect to the preceding section so that the flow pattern is altered as the fluids move from section to section.

The static mixer used herein is designed to effect distribution of reactant gas with reactant liquid through gas bubble size control. Bubble sizes range from 0.1–15 mm in diameter. Bubble size targets range from 0.5 to 5 times the channel width or hydraulic diameter of the cell, preferably 1–3 times the channel width, are employed for monolith catalytic reactors where the cells per square inch (cpi) range from 100 to 1200, preferably 200 to 600 cpi. (Hydraulic diameter of the cell is defined as 4 times the cross-sectional area of a channel or cell divided by its wetted perimeter.) Bubble size control is largely dictated by the design of the channels in the static mixer and by control of fluid velocity through the static mixer.

Bubble size can be predetermined by using published information equating gas and liquid flow rates through the static mixer. Typically, air and water are used in such test procedures and bubble size determination based on air/water mixture is deemed to correlate to the bubble size of the reactant gas and reactant liquid under operating conditions. Alternatively there are ways to measure bubble size in the reactor, such as computer tomography or through the use of laser analyzers. To obtain uniformity of reaction, calibration of the monolith catalytic reactor should be effected by measurement of the bubble size.

Monolith catalysts employed in the process described herein consist of an inorganic porous substrate, a metallic substrate, or a modified substrate, i.e., a monolith support, coated with a catalytic metal. The modification can be a coating derived from a carbon or a heat-treated network polymer. Often the monoliths are based upon a honeycomb of long narrow capillary channels, circular, square, rectangular or other geometric shape, whereby gas and liquid are co-currently passed through the channels under a laminar flow regime.

The flow of gas and liquid in these confined channels and under these conditions promote the desired "Taylor" flow with bubbles of $H_2$ gas squeezing past the liquid. This capillary action promotes very high gas-liquid and liquid-solid mass transfer. Taylor flow of a gas/liquid system is such that the gas bubbles are of substantially uniform size and surrounded by a thin film of liquid.

FIG. 3 illustrates the differences in bubble characteristics under different flow regimes. The objective is to produce substantially uniform gas bubbles surrounded by a thin liquid film as in view (d). Other views, such as, (a), (b), and (c) show varying gas bubble size with small bubbles surrounded by large quantities of liquid to the very large bubbles such as (e), (f), (g), and (h) surrounded by insufficient reactant liquid.

The pressure drop within an effective monolith catalytic reactor can range from 2 kPa/m to 200 kPa/m for combined gas/liquid superficial velocities between 0.1 to 2 meters/second for 50% gas holdup in a monolith catalytic reactor having 400 cpi (cells per square inch). Typical dimensions for a honeycomb monolith cell wall spacing range from 0.5 to 5 mm between the plates. Alternatively, the monolith may have from 100 to 1200, preferably 200 to 600 cpi. Channels may be square, hexagonal, circular, elliptical, etc. in shape.

Catalytic metals suited for reaction obviously depend upon the type of reaction to be effected. For example, hydrogenation of organic compounds utilize catalytic metals which are impregnated or directly coated onto the monolithic substrate, a modified substrate or a washcoat. The catalytic metals include those of Group VIb, Group VIIb, Group VIII, and Group Ib of the periodic table and conventionally used in hydrogenation reactions. Examples of catalytic metal components include cobalt, nickel, palladium, platinum, copper, rhodium, ruthenium, rhenium, iridium, and so forth. Often a mixture of metals are employed, one example being palladium and nickel. For a monolith catalyst impregnated with a washcoat the composition of catalytic metals is typically identified as a weight percent within the washcoat itself. The washcoat may be applied in an amount of from 1 to 50% of the monolith total weight. Typical catalyst metal loadings, then, range from 0.1 to 25% by weight and preferably from 1 to 20% by weight of the washcoat. The catalytic metals may be incorporated into the monolith in a manner generally recognized by the art. Incipient wetness from a salt solution of the catalytic metal is one example of a method for incorporating a metal catalytic component on the monolith substrate or modified monolith.

In certain hydrogenation reactions involving immiscible liquid phases, a monolith substrate, e.g., inorganic or carbon based, may be coated with a network polymeric film with that film acting as a support for the metal. Eliminating microporosity of the carbon surface of the polymeric film is advantageous for fast reaction rates and long catalyst life when immiscible liquid phases are present. Small and medium size pores in the surface tend to lead to catalyst deactivation through pore plugging with high molecular weight co-products. Therefore, the carbon monolith, a carbon coated monolith or a polymer network/carbon coated monolith should have a very low surface area for optimum activity, i.e., a $N_2$ BET of from approximately 1 to 15 $m^2$/gram of total surface area of monolith catalyst.

To achieve a polymer network/carbon coated monolith having low surface area, polymer coating solutions may be applied to the wall surface and heated below traditional carbonization temperatures. Examples of polymer solutions include furfuryl alcohol and furfuryl alcohol with other additives such as pyrrole and polyethylene glycol methyl ether; epoxy resins with amines; epoxy resins with anhydrides; saturated polyester with glycerol or other multifunctional alcohols; oil-modified alkyd saturated polyesters, unsaturated polyesters; polyamides; polyimides; phenol/formaldehyde; urea/formaldehyde; melamine/formaldehyde and others. The above procedure can be modified by using a commercially available oligomer or copolymer of furfuryl alcohol.

Carbonization of the polymer coating is effected at relatively low temperature. Temperatures for carbonization range from 250 to 350° C. vs. 550–900° C. commonly used in the prior art.

Numerous types of reactions can be effected in the monolith catalytic reactor but primarily hydrogenation and oxidation are the key reactions. Hydrogenation of a wide variety of compounds can be effected, e.g., nitroaromatics, nitriles, unsaturated organics e.g. unsaturated amines. Organic compounds having functional groups can be hydrogenated via a condensation reaction. Preferred compounds are the nitroaromatic compounds and these include nitrobenzene, nitrotoluenes, nitroxylenes, nitroanisoles and halogenated nitroaromatics where the halogen is Cl, Br, I, or F.

To facilitate an understanding of the operation of the static mixer/monolith catalytic reactor combination, reference is made to FIG. 1. Static mixer 1 is comprised of a plurality of sections 3 and is coupled to a monolith catalytic reactor 4. Reactant gas, reactant liquid and, optionally a recycle, is introduced to a cross via inlet lines 5, 7 and 9. The three fluids are mixed slightly in the cross and withdrawn through line 11. At that point they are introduced to the inlet of the static mixer. As the fluids pass through the static mixer they are directed in an alternating angular flow path as they pass through the plurality of sections. As shown, the initial section is oriented about the longitudinal axis of the flow path from the next contiguous section, e.g., 3a (shown by the space between the initial section 3 and the next contiguous section 3a). A frothy mixture of gas and liquid is withdrawn through outlet 13 (as shown by the small space between the last section 3 of static mixer 1 and monolith catalytic reactor 4) which is of sufficient width to provide a reliable even distribution of the resulting gas/liquid froth to the cross section of monolith catalytic reactor 4. Even distribution allows all regions of monolith catalytic reactor 4 to achieve Taylor flow on a consistent basis and thereby achieve higher mass transfer rates than would otherwise be available. Reaction takes place in the plurality of cells 15. Reaction product is removed from monolith catalytic reactor 4 via line 17 for recovery of product and unreacted materials.

Figure 2:
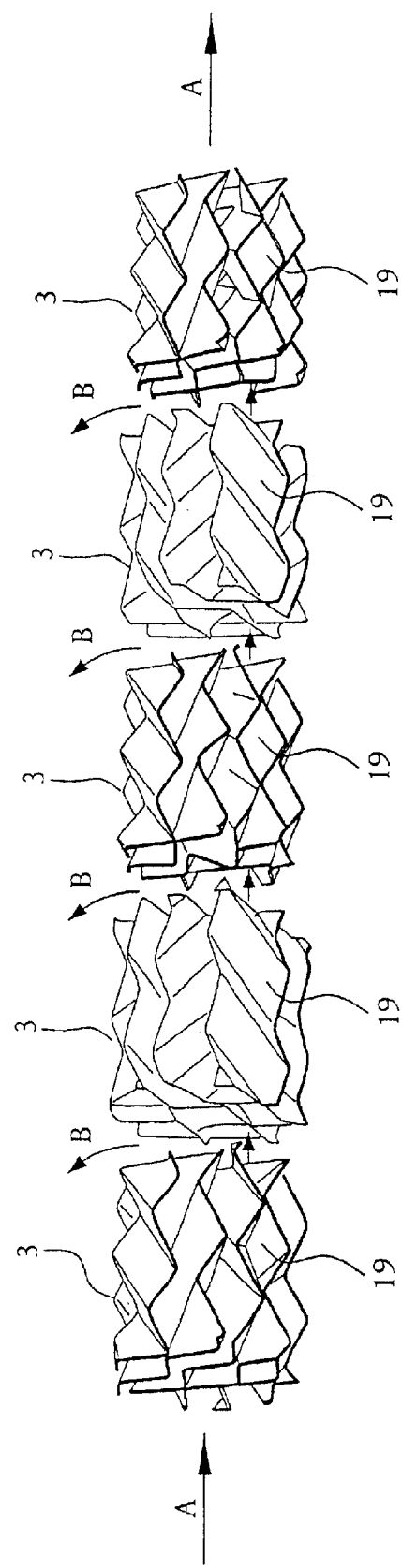
FIG. 2 is an isometric view of a static mixer showing the interengaging and intersecting corrugations and flow patterns of the separate mixing elements.
Figure 3H:
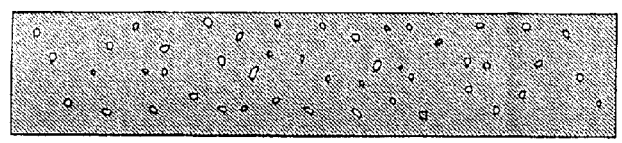
FIG. 3 is a view in cross-section illustrating flow regimes of reactant gas and reactant liquid under various conditions in the capillaries of a monolith catalytic reactor.
Figure 3G:
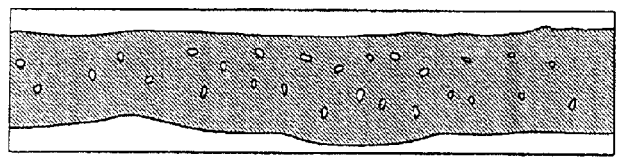
Figure 3F:
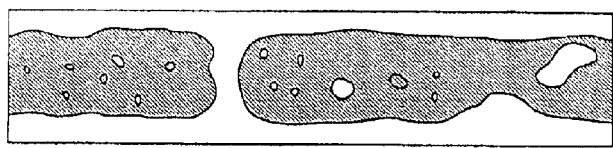
Figure 3E:
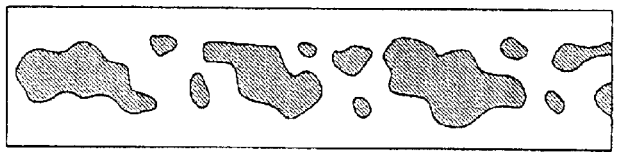
Figure 3D:
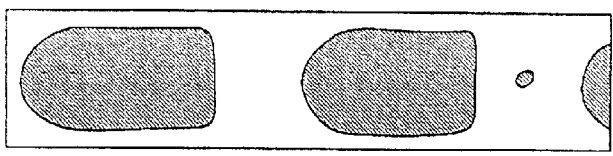
Figure 3C:
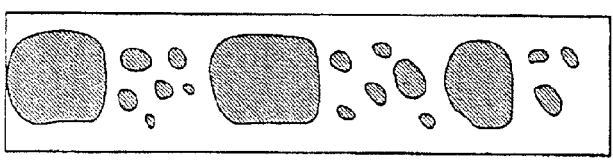
Figure 3B:
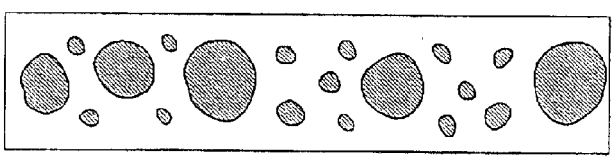
Figure 3A:
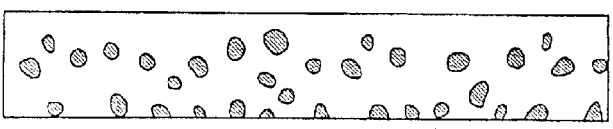

FIG. 2 is an isometric view of static mixer 1 having a plurality of mixing sections 3. The flow pattern is such that substantially parallel channels 19 guide a mixture of reactant gas and reactant liquid through each section, first angularly radially outward then inward as they proceed in the flow direction (as indicated by arrows A) along the longitudinal axis of the static mixer from inlet to outlet. At the intersection points of the channels, the fluids, because of the turbulence created, become mixed in greater degree than would be achieved in a straight through flow pattern. To further enhance the mixing process, each section is rotated, typically from 45 to about 90°, and shown by the arrows B from a preceding section in the flow path around the longitudinal axis of static mixer 1 so that there is flow reversal from section to section.

The following examples are provided to illustrate various and preferred embodiments of the invention and are not intended to restrict the scope thereof.

EXAMPLE 1

Hydrogenation of Dinitrotoluene in System Comprised of Static Mixer and Monolith Catalytic Reactor In carrying out the hydrogenation of dinitrotoluene, a reactor comprised of a cylindrical monolith reactor bed, approximately 100" high and 1" in diameter is used. The catalyst bed is made from a commercial 400 cells per square inch (cpi) cordierite monolith support having square shaped cells with a 25% alumina washcoat and a catalyst metal loading of 20% Ni and 1% Pd based on the washcoat. The reactor system is set up similar to FIG. 1 with the excess hydrogen gas being recycled to the inlet of the reactor using a compressor.

Hydrogen is fed in excess of the stoichiometric requirement for dinitrotoluene hydrogenation. The dinitrotoluene is continuously fed as a molten liquid and no solvent is employed. Both the dinitrotoluene feed and the recycled hydrogen are fed into the recycled reaction mixture at the entrance to the static mixer at a mixing "cross."

In this demonstration, the static mixer used is Model No. 1"L4B8 consisting of 8 type SMVL elements, each 1" long by 1" in diameter and manufactured by Koch-Glitsch, Inc. The SMVL static mixer accomplishes intimate mixing in a short length of pipe with a minimal pressure drop. This style of mixer is appropriately designed for low viscosity liquid/liquid mixing, gas/liquid mixing, and immiscible fluid dispersions and consists of stacked corrugated sheets oriented to give a large number of intersecting flow channels.

The toluenediamine and water product are continuously removed from the reactor system. The operating conditions of the runs below were selected from air/water data to obtain Taylor flow. Gas and liquid superficial velocities in the range of 30–35 cm/sec respectively are employed in the monolith channels. Typically, the inlet dinitrotoluene (DNT) concentration is maintained in the 0.5–2 wt % range to accomplish >90% conversion of DNT across the monolith bed and to limit the adiabatic temperature rise of the reaction mixture. The inlet temperature is also adjusted to accomplish this reaction rate.

The static mixer used is designed to provide the desired hydrogen bubble size of 1 to 3 mm. uniformly across the reactor cross section to obtain the gas-liquid mass transfer rates needed to support this vigorous reaction. If a bulk hydrogen concentration is assumed to be zero, then the minimum average gas-liquid mass transfer coefficient, $k_L a$, is 1 sec$^{-1}$. In actuality, the bulk hydrogen concentration is rarely driven to zero in such operations, so the average $k_L a$ is expected to be in the range of 2–5 sec$^{-1}$, an excellent result. This is evidence that the static mixer is providing the necessary flow conditions and both DNT and hydrogen bubble distribution to support commercially practical reaction rates. The pressure drop across the static mixer is generally less than 2 psig, and the pressure drop across the entire monolith bed is less than 15 psig, which also increases the practicality of this process by reducing the power input needed for the liquid recycle pump and recycle hydrogen compressor.

Each of the feed streams are passed upflow through the static mixer and into the monolith catalytic reactor. Reaction product containing product and unreacted feed is recovered from the reactor. Unreacted components in the reaction product are recycled to the static mixer and then through the reactor. The following table sets forth conditions for representative runs.

| Run | Average Recycle Liquid Rate (gph)[1] | Average Recycle Hydrogen Rate (acfh)[2] | Average DNT Feed Rate (grams/min) | Reactor Inlet Pressure (psig) | Reactor Inlet Temperature (° C.) | Reactor Outlet Temperature (° C.) | Time on-stream (hr) | Average DNT Conversion (%) |
|---|---|---|---|---|---|---|---|---|
| 1 | 70 | 12 | 30 | 600 | 136 | 147 | 40 | 99 |
| 2 | 65 | 10 | 45 | 600 | 135 | 150 | 50 | 97 |
| 3 | 64 | 13 | 40 | 600 | 132 | 147 | 50 | 99 |

[1] gph refers to gallons/hour.
[2] acfh refers to actual cubic feet/hour.

As can be seen, excellent DNT conversions are obtained without process excursions over an extended period of time.

When the process is operated in the absence of a static mixer, there is substantial difficulty in the start-up to obtain Taylor flow in the monolith catalytic reactor. Numerous process excursions are observed thereby making the process unsatisfactory from a safety point of view and from a production point of view.

What is claimed is:

1. In a process for the heterogeneous catalytic reaction of a mixture of a reactant gas and reactant liquid in a monolith catalytic reactor under conditions of reaction, the improvement which comprises initially mixing the reactant gas with the reactant liquid in a static mixer thereby forming a frothy mixture, introducing the resultant frothy mixture into the monolith catalytic reactor for reaction, and, then, recovering reaction product from the monolith catalytic reactor.

2. The process of claim 1 wherein the monolith catalytic reactor has from 100 to 1200 cells per square inch.

3. The process of claim 2 wherein the frothy mixture is passed upflow through said monolith catalytic reactor at a superficial velocity of from 0.1 to 2 meters per second.

4. The process of claim 3 wherein the static mixer is comprised of a plurality of sections, each section comprised of a tubular housing having a flow direction along an axis carrying a plurality of stationary, rigid elements that form interengaging and intersecting channels in the flow direction and which extend angularly to the longitudinal axis.

5. The process of claim 4 wherein the static mixer is comprised of a plurality of mixing sections with each mixing section rotated about the longitudinal axis in the direction of flow from the preceding section.

6. The process of claim 5 wherein the alternating parallel channels intersect at angles from 45 to about 90 degrees to the longitudinal axis.

7. The process of claim 6 wherein a plurality of sections in the static mixer are rotated from about 45 to 90 degrees about the longitudinal axis from the preceding section in the direction of flow.

8. The process of claim 7 wherein the bubble size of reactant gas is from 0.5 to 5 times the cell width or hydraulic diameter and the monolith catalytic reactor has from 200 to 600 cells per square inch.

9. The process of claim 8 wherein the organic compound used in the hydrogenation reaction is selected from the group consisting of a nitroaromatic, a nitrile, an unsaturated organic, and reaction products of a ketone or aldehyde with ammonia or a primary or secondary amine.

10. The process of claim 9 wherein the organic compound is a nitroaromatic compound.

11. The process of claim 10 wherein the nitroaromatic compound is nitrobenzene, a nitrotoluene, a nitroxylene, a nitroanisole and a halogenated nitroaromatic wherein halogen in the halogenated nitroaromatic is Cl, Br, I, or F.

12. The process of claim 7 wherein the nitroaromatic compound is dinitrotoluene.

* * * * *